(12) United States Patent
Davies et al.

(10) Patent No.: US 8,979,791 B2
(45) Date of Patent: Mar. 17, 2015

(54) MEDICATED MODULE WITH NEEDLE GUARD

(75) Inventors: James Alexander Davies, Leamington Spa (GB); Steven Wimpenny, Leamington Spa (GB); Daniel Thomas De Sausmarez Lintell, Rugby (GB); Malcolm Stanley Boyd, Wellesbourne (GB); Naceur Rekaya, Leamington Spa (GB); Simon Lewis Bilton, Leamington Spa (GB); John David Cross, Northhampton (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 45 days.

(21) Appl. No.: 13/322,096

(22) PCT Filed: Jun. 1, 2010

(86) PCT No.: PCT/EP2010/057583
§ 371 (c)(1),
(2), (4) Date: Jan. 31, 2012

(87) PCT Pub. No.: WO2010/139675
PCT Pub. Date: Dec. 9, 2010

(65) Prior Publication Data
US 2012/0123346 A1 May 17, 2012

Related U.S. Application Data

(60) Provisional application No. 61/183,457, filed on Jun. 2, 2009.

(30) Foreign Application Priority Data

Jul. 25, 2009 (EP) .................................... 09009663

(51) Int. Cl.
*A61M 37/00* (2006.01)
*A61M 5/28* (2006.01)
(Continued)

(52) U.S. Cl.
CPC ............... *A61M 5/284* (2013.01); *A61M 5/326* (2013.01);
(Continued)

(58) Field of Classification Search
USPC ................. 604/110, 181, 187, 195, 200–201, 604/203–206, 218, 220, 231–238, 244, 604/82–92, 191, 192, 197, 198, 199, 207, 604/213, 407, 411–415, 131, 134–136, 138, 604/139, 146, 228, 263, 137, 93.01, 141, 604/142–144, 147, 149, 140, 70, 81
See application file for complete search history.

(56) References Cited

U.S. PATENT DOCUMENTS

| 3,811,441 A | 5/1974 | Sarnoff |
| 5,281,198 A | 1/1994 | Haber et al. |

(Continued)

FOREIGN PATENT DOCUMENTS

| CN | 1509192 | 6/2004 |
| DE | 102006041809 | 3/2008 |

(Continued)

OTHER PUBLICATIONS

European Search Report for EP Application No. 09009663, dated Nov. 30, 2009.

(Continued)

*Primary Examiner* — Scott Medway
(74) *Attorney, Agent, or Firm* — McDonnell Boehnen Hulbert & Berghoff LLP

(57) ABSTRACT

A medicated module comprising a connecting body configured for attachment to a drug delivery device. A first needle is fixed within the connecting body and an outer body operatively coupled to the connecting body. A needle guard operatively coupled to the outer body and a biasing member positioned between the outer body and needle guard. A second needle fixed within the outer body and a recess within the connecting body defines a reservoir. The reservoir contains at least one dose of a medicament and is configured for fluid communication with the first and second needle.

10 Claims, 7 Drawing Sheets

(51) Int. Cl.
*A61M 5/32* (2006.01)
*A61M 5/20* (2006.01)
*A61M 5/315* (2006.01)
*A61M 5/34* (2006.01)
*A61M 5/178* (2006.01)
*A61M 5/31* (2006.01)

(52) U.S. Cl.
CPC ............ *A61M 5/204* (2013.01); *A61M 5/288* (2013.01); *A61M 5/31525* (2013.01); *A61M 5/3294* (2013.01); *A61M 5/3297* (2013.01); *A61M 5/347* (2013.01); *A61M 2005/1787* (2013.01); *A61M 2005/3142* (2013.01); *A61M 2005/3247* (2013.01); *A61M 2005/3267* (2013.01)
USPC ............ 604/82; 604/110; 604/181; 604/187; 604/195; 604/200; 604/203; 604/218; 604/220; 604/231; 604/92; 604/191; 604/207; 604/93.01; 604/141

(56) References Cited

U.S. PATENT DOCUMENTS

| | | | | |
|---|---|---|---|---|
| 5,330,426 | A | * | 7/1994 | Kriesel et al. .................. 604/89 |
| 5,562,616 | A | * | 10/1996 | Haber et al. .................. 604/82 |
| 6,071,270 | A | * | 6/2000 | Fowles et al. ................. 604/413 |
| 6,210,369 | B1 | * | 4/2001 | Wilmot et al. ................. 604/157 |
| 6,562,002 | B1 | * | 5/2003 | Taylor ............................ 604/82 |
| 6,607,508 | B2 | * | 8/2003 | Knauer .......................... 604/131 |
| 2002/0123719 | A1 | * | 9/2002 | Lavi et al. ...................... 604/82 |
| 2002/0177819 | A1 | * | 11/2002 | Barker et al. ................. 604/232 |
| 2003/0055376 | A1 | * | 3/2003 | Delay ............................. 604/82 |
| 2005/0277895 | A1 | * | 12/2005 | Giambattista et al. ........ 604/198 |
| 2006/0229562 | A1 | | 10/2006 | Marsh et al. |
| 2006/0276755 | A1 | | 12/2006 | Sullivan et al. |
| 2009/0018506 | A1 | | 1/2009 | Daily et al. |

FOREIGN PATENT DOCUMENTS

| | | |
|---|---|---|
| JP | H01-500803 | 3/1989 |
| JP | 2005-516691 | 6/2005 |
| WO | 88/02265 | 4/1988 |
| WO | 94/11056 | 5/1994 |
| WO | 02/072173 | 9/2002 |
| WO | 03/066141 | 8/2003 |
| WO | 2004/108205 | 12/2004 |
| WO | 2008/140737 | 11/2008 |

OTHER PUBLICATIONS

International Search Report and Written Opinion for International App. No. PCT/EP2010/057583, completed Aug. 31, 2010.
International Preliminary Report on Patentability for International App. No. PCT/EP2010/057583, completed Sep. 16, 2011.
Translation of Chinese Office Action for Chinese Patent Application No. 201080030153.0, dated Jul. 15, 2013.
English translation of Japanese Office Action for JP App. No. 2012-513588, mailed May 20, 2014.

* cited by examiner

MEDICATED MODULE WITH NEEDLE GUARD

CROSS REFERENCE TO RELATED APPLICATIONS

The present application is a U.S. National Phase Application pursuant to 35 U.S.C. §371 of International Application No. PCT/EP2010/057583 filed Jun. 1, 2010, which claims priority to U.S. Provisional Patent Application No. 61/183,457 filed on Jun. 2, 2009 and European Patent Application No. 09009663.7 filed on Jul. 25, 2009. The entire disclosure contents of these applications are herewith incorporated by reference into the present application.

FIELD OF THE INVENTION

According to a preferred embodiment, the present disclosure relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers, or packages, each containing independent (single drug compound) or pre-mixed (co-formulated multiple drug compounds) drug agents. One aspect of our present application is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. This invention may be of particular benefit where combination therapy is desirable, but not possible in a single formulation for reasons such as, but not limited to, stability, compromised therapeutic performance and toxicology.

For example, in some cases it might be beneficial to treat a person suffering from diabetes with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two or more active medicaments or "agents" simultaneously. The two or more active agents may interact with each other during the long-term, shelf life storage of the formulation. Therefore, there are certain advantages to storing the active components separately and only combine them at the point of delivery, e.g. injection, need-less injection, pumps, or inhalation. However, the process for combining the two agents needs to be simple and convenient for the user to perform reliably, repeatedly and safely.

A further concern is that the quantities and/or proportions of each active agent making up the combination therapy may need to be varied for each user or at different stages of their therapy. For example, one or more active agents may require a titration period to gradually introduce a patient to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional concerns arise where a multi-drug compound therapy is required, because certain users cannot cope with having to use more than one drug delivery system or make the necessary accurate calculation of the required dose combination. This is especially true for users with dexterity or computational difficulties.

Other problems arise where a user may attempt to re-use a non-sterile needle after a certain dose combination has been delivered. Using such a non-sterile needle could lead to the transmission of certain diseases (septicaemia) and therefore there exists a need for a medicated module that prevents needle re-use. There is a further concern of inadvertent needle sticks with certain needle assemblies where the injection needle is not concealed or covered, especially after use when a needle may be contaminated with blood. As such, there is also a general need to reduce certain patient's needle anxiety that may heighten a patient's fear or phobia of exposed needles.

Accordingly, there exists a strong need to provide devices and methods for the delivery of two or more medicaments in a single injection or delivery step that is simple and safe for the user to perform and that also tends to reduce a patient's anxiety towards injections or needles. The present application discloses specific embodiments of methods, devices and drug delivery kits that overcome the above-mentioned concerns by providing separate storage containers for two or more active drug agents that are then only combined and/or delivered to the patient during a single delivery procedure. According to a preferred embodiment of the invention, such devices may be provided in separate storage containers or provided in a kit form comprising at least one medicated module and at least one non-medicated module.

According to the disclosure the term medicated module is preferably used to characterize a needle sub-assembly comprising a containment or reservoir of a (secondary) drug compound. Consequently, a non-medicated module is preferably characterized as a needle sub-assembly, however without having a containment or reservoir of a (secondary) drug compound. As such the medicated module and/or the non-medicated module may comprise at least one double ended needle. Furthermore the medicated module and/or the non-medicated module may comprise a needle guard. The medicated module and/or the non-medicated module may be configured to be attachable to a drug delivery device, e.g. a pen-type drug delivery device.

According to a specific embodiment described in the following, setting a dose of one medicament automatically fixes or determines the dose of the second medicament (i.e., a non-user settable dose). The present application may also give the opportunity for varying the quantity of one or both medicaments. For example, one fluid quantity can be varied by changing the properties of the injection device (e.g., dialing a user variable dose or changing the device's "fixed" dose). The second fluid quantity can be changed by manufacturing a variety of secondary drug containing packages or kits with each variant containing a different volume and/or concentration of the second active agent. The user or healthcare professional would then select or prescribe the most appropriate secondary package or series or combination of series of different packages or kits for a particular treatment regime.

These and other advantages will become evident from the following more detailed description of the invention.

SUMMARY

The general problem to be solved by the present invention is to provide a medicated module, a drug delivery kit and drug delivery system where the administration of a medicament is improved.

According to some specific embodiments, the present application discloses modules, systems, methods, and drug delivery kits that allow for the complex combination of multiple drug compounds within a single drug delivery system. Preferably, such a system includes a needle guard that functions to prevent needle reuse and that can also function to reduce needle phobia while also reducing potential inadvertent needle sticks.

According to a specific embodiment, a user can set and dispense a multi-drug compound device through one single dose setting mechanism and a single drug dispense interface. Preferably, the single drug dispense interface may then be locked out so as to prevent reuse of a medicated module (i.e., re-use of the injection needle). Preferably, the single dose setter controls the mechanism of the device such that a predefined combination of the individual drug compounds is delivered when a single dose of one of the medicaments is set and dispensed through the single drug dispense interface. The term drug dispense interface preferably is, in the context of this disclosure, any type of outlet that allows the two or more medicaments to exit the drug delivery system and be delivered to the patient. In a preferred embodiment the single drug dispense interface comprises a hollow needle cannula.

By defining the therapeutic relationship between the individual drug compounds some embodiments of the presently disclosed delivery devices and systems would help ensure that a patient/user receives the optimum therapeutic combination dose from a multi-drug compound device without the inherent risks associated with multiple inputs where the user has to calculate and set the correct dose combination every time they use the device. The combination of the individual medicaments comprises preferably at least two different drug agents, wherein each medicament comprises at least one drug agent. The medicaments can be fluids, defined herein as liquids or gases that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, the present application is of particular benefit to patients with dexterity or computational difficulties as the single input and associated predefined therapeutic profile removes the need for them to calculate their prescribed dose every time they use the device and the single input allows considerably easier setting and dispensing of the combined compounds. This application may also be of particular benefit to patients experiencing needle phobia or who may experience a general fear of inadvertent needle sticks.

In a preferred embodiment a primary or master drug compound or medicament, such as insulin, contained within a multiple dose, user selectable device could be used with a single use, user replaceable, module that contains a single dose of a secondary medicament and the single dispense interface. When connected to the primary device the secondary medicament is activated/delivered on dispense of the primary medicament. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one embodiment, the present patent application relates to a medicated module attachable to a drug delivery device. The medicated module comprises a connecting body configured for attachment to the drug delivery device. A first needle is fixed within the module or, according to a specific embodiment, within the connecting body. Furthermore, an outer body may operatively be coupled to the connecting body. A needle guard is operatively coupled to the module or, according to a specific embodiment, to the outer body. A biasing member or element is positioned to bias the needle guard. The biasing member may be positioned between the outer body and the needle guard. A second needle is fixed within the module or, according to a specific embodiment, within the outer body. A reservoir containing at least one dose of a medicament is provided. The reservoir may be defined by a recess within the connecting body. The reservoir may alternatively be defined by a capsule, i.e. a self-contained sealed reservoir of a secondary medicament. The reservoir is configured for fluid communication with the first and the second needle.

In another arrangement, a drug delivery kit for a drug delivery device comprises a medicated module configured for connection to the drug delivery device. A non-medicated module may also be provided and is configured for connection to the drug delivery device. In one arrangement, the drug delivery kit comprises a plurality of medicated modules configured for connection to said drug delivery device. In one arrangement comprising a plurality of modules, each module comprises a medicament having a different titration level than the next medicated module. In an alternative arrangement, the drug delivery kit comprises a plurality of non-medicated modules.

A drug delivery device preferably comprises a (primary) reservoir of medicament containing at least one drug agent, a dose setter, a dose button, and a delivery mechanism. The dose button is operably connected to the primary reservoir. The dose setter is operably connected to the primary reservoir. The delivery mechanism may be of any type utilizing a rotatable piston rod, preferably a rotatable piston rod with two distinct threads.

A particular benefit of our application is that the medicated module makes it is possible to tailor dose regimes when required, especially where a titration period is necessary for a particular drug. The medicated module could be supplied in a number of titration levels with differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules or a kit of modules and then when these were finished, the physician could then prescribe the next level or the next drug delivery kit. One advantage of this titration program is that the primary device can remain constant.

In a preferred embodiment, the primary drug delivery device is used more than once and therefore is multi-use. Such a device may or may not have a replaceable reservoir of the primary drug compound, but our invention is equally applicable to both scenarios. It is possible to have a suite of different medicated modules for various conditions that could be prescribed as one-off extra medication to patients already using a standard drug delivery device (or family of devices). Should the patient attempt to reuse a previously used medicated module, the presently disclosed medicated module provides a lockable needle guard feature that could alert the patient to this situation. Other means of alerting the user may include some (or all) of the following:

1. Physical prevention of medicated module re-attachment to the primary drug delivery device once the module was used and removed.
2. Physical prevention of insertion of the used drug dispense interface into the patient (e.g., a single use needle-guard type arrangement).
3. Physical/hydraulic prevention of subsequent liquid flow through the drug dispense interface once it has been used.
4. Physical locking of the dose setter and/or dose button of the primary drug delivery device.
5. Visual warnings (e.g., change in color and/or warning text/indicia within an indication window on the module once needle insertion and/or fluid flow has occurred).
6. Tactile feedback (presence or absence of tactile features on the outer surface of the module hub following use).

A further feature of this embodiment is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant.

A further aspect of the invention relates to a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

In addition, a drug delivery system is provided to deliver two or more medicaments operable through a single dispense interface. The system comprises a primary reservoir of medicament containing at least one drug agent for example a liquid medicament such as insulin or an analog thereof as well as a dose button operably connected to the primary reservoir of medicament. Furthermore, the drug delivery system may comprise a housing having a single dose setter operably connected to the primary reservoir of medicament. Furthermore, a single drug dispense interface configured for fluid communication with the primary reservoir is provided. The system has a medicated module comprising a needle guard and a secondary reservoir of medicament containing at least one drug agent. The system is designed such that a single activation of the dose button causes medicament from the primary reservoir and the second medicament from the secondary reservoir to be expelled through the single drug dispense interface. Preferably, the primary reservoir contains a liquid medicament. According to a specific embodiment, the single activation of the dose button causes a non-user settable dose of the second medicament to be expelled. The medicated module may be primable and may, in addition, contain a sealed sterile capsule containing a single dose of at least one drug agent. I.e. the medicated module may comprise a reservoir comprising a capsule being the self-contained sealed reservoir of a (secondary) medicament. In this case a single activation of the dose button will cause to expel the single dose of the capsule.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

According to a specific embodiment, the present invention administers a fixed predetermined dose of a second medicament (secondary drug compound) and a potentially variable dose of a first medicament (primary drug compound) through a single output or drug dispense interface such as a double ended needle. Setting the dose of the primary medicament by the user may automatically determine the fixed dose of the second medicament. This fixed dose of the second medicament is preferably a single dose. In a preferred arrangement, the drug dispense interface comprises a needle cannula (hollow needle) and a needle guard that may be locked out after medicament injection.

Figure 1:
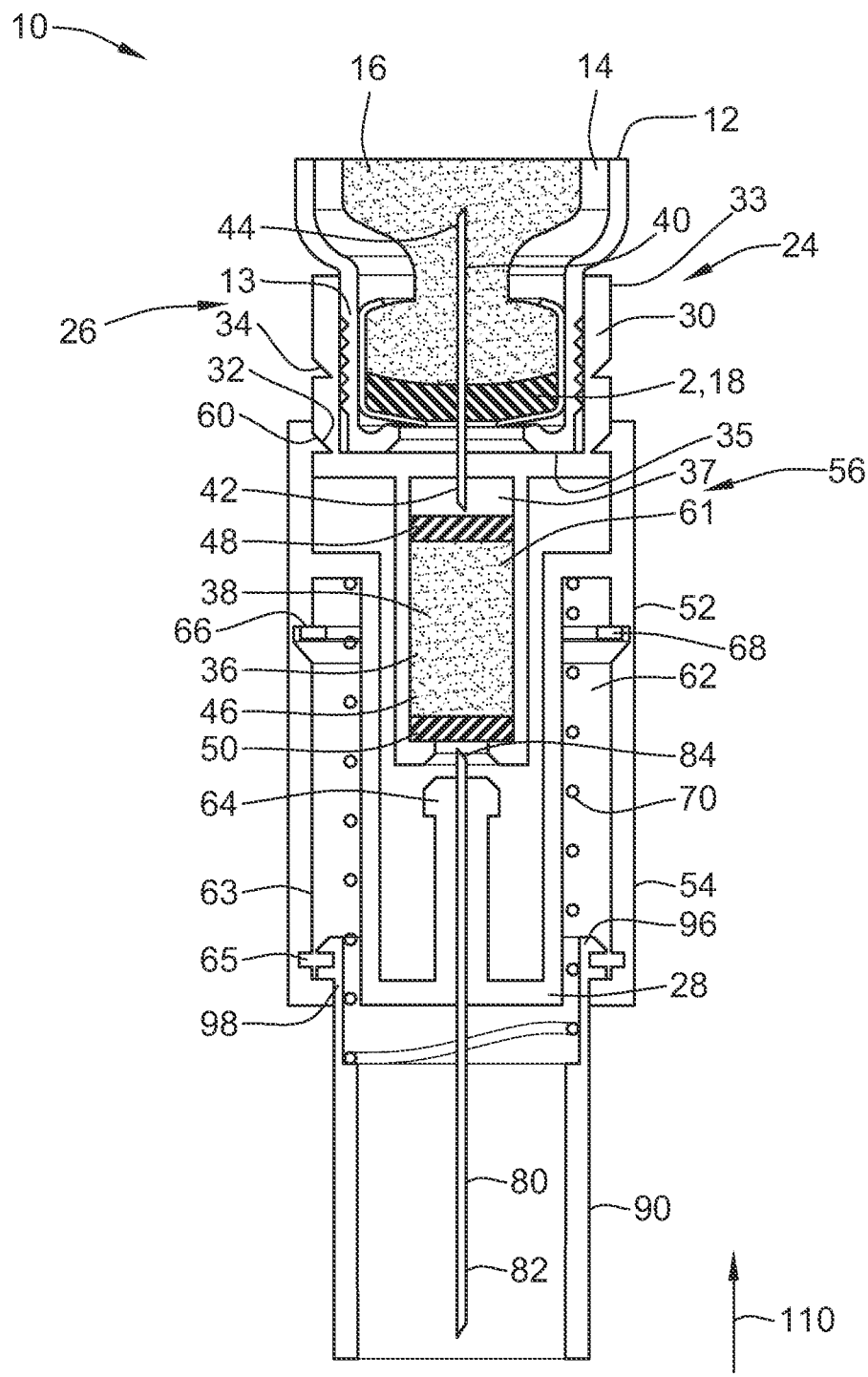
FIG. 1 illustrates a sectional view of one arrangement of a medicated module attached to a drug delivery device.

FIG. 1 illustrates a preferred arrangement of a medicated module 10 where a first needle 40 pierces a septum 2 of a device cartridge 14. A second injection needle 80 may be used to subcutaneously inject the first medicament contained in the cartridge along with a second medicament contained in the medicated module. Located between the two needles 40, 80 is a recess 37 defined by a connection body 24. Preferably, this recess contains a reservoir of a second medicament 38. Most preferably, this reservoir comprises a capsule 46 that has ends sealed with first and a second pierceable seals 48, 50, respectively.

In this preferred arrangement, the medicated module 10 as illustrated is attached to a drug delivery device 12. Only a portion of such a drug delivery device is illustrated in FIG. 1. The drug delivery device 12 may comprise a cartridge holder containing a standard cartridge 14. This standard cartridge 14 comprises a first medicament 16 such as insulin or the like.

In one arrangement, the medicated module 10 is preferably self-contained and may be provided as a sealed and sterile disposable module. Such a module comprises an attachment means compatible to the attachment means at a distal end of the drug delivery device 12. Although not shown, the medicated module 10 could be supplied by a manufacturer contained in a protective and sterile container where the user would peel or rip open a seal or the container itself to gain access to the sterile medicated module. In some instances it might be desirable to provide two or more seals for each end of the medicated module. In addition, and as will be explained in detail below, in one arrangement, such medicated module 10 may be provided in a drug delivery kit along with at least one non-medicated module, such as the module illustrated in FIG. 5.

Figure 9:
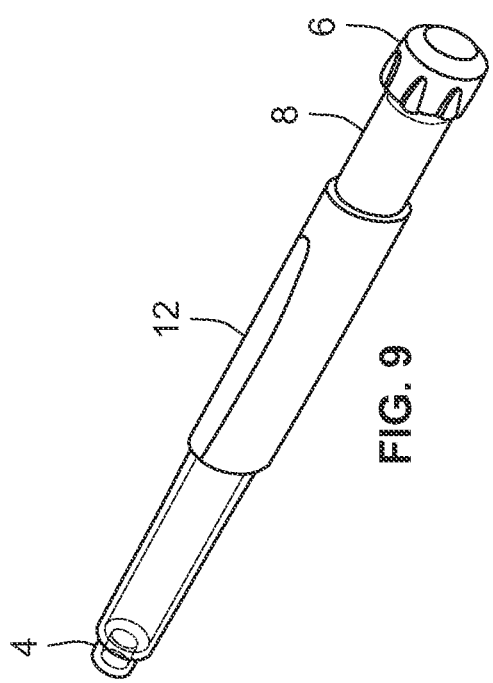
FIG. 9 illustrates one possible drug delivery device that can be used with the medicated module illustrated in FIG. 1.

One example of a drug delivery device 12 is illustrated in FIG. 9. Any known attachment means can be used, including permanent and removable connection means. Threads, snap locks, snap fits, luer locks, bayonet, snap rings, keyed slots, and combinations of such connections can be used to attach module 10 to device 12. As just one example, FIG. 1 illustrates the attachment means comprising screw threads. The arrangement shown in FIG. 1 has the benefit of the second medicament 38 as a single dose being contained entirely within the medicated module 10. This can minimize the risk of material incompatibility between the second medicament and the materials used in the construction of the medicated module 10.

Returning to FIG. 1, the medicated module 10 comprises a connecting body 24, a first needle 40, an outer body 52, a second needle 80, a biasing member 70, and a needle guard 90.

The connecting body 24 extends from a proximal end 26 to a distal end 28. The proximal end of the connecting body is provided with a connector 30 so that the medicated module 10 may be connected to the drug delivery device 12. Preferably, this connector is provided along an inner surface 22 of the connecting body 24 and provides a releasable connection to the drug delivery device 12. Such a releasable connector may comprise a snap fit, form fit, snap lock, luer lock or other similar connection mechanism known to those of skill in the art. As can also be seen from FIG. 1, the connecting body 24 further comprises a first and second recess 32, 34. These recesses are provided along a connector body external surface 33. Although only two recesses 32, 34 are illustrated in the medicated module 10 arrangement illustrated in FIG. 1, alternative recess arrangements may comprise more or less than two recesses 32, 34. As will be explained in greater detail below, as illustrated in FIG. 1, a male member 60 of an outer body 52 is releasably engaged to the first recess 32.

The connecting body 24 defines a reservoir 36 and preferably this reservoir contains a second medicament 38. Most preferably, this second medicament 38 comprises a single dose of a medicament, such as a single dose of GLP-1 or alternatively a pre-mix of medicaments. In one preferred arrangement, the reservoir comprises a capsule 46 comprising a first and a second end that is sealed with pierceable membranes 48, 50. Such a construction provides a hermetically sealed reservoir for the second medicament 38.

The connecting body 24 further comprises a first needle 40 rigidly affixed in an upper surface 35 of the connecting body. Preferably, this first needle 40 comprises a double ended needle having a first piercing end 42 (i.e., a distal end) and a second piercing end 44 (i.e., a proximal end). In this preferred arrangement, when the medicated module 10 is initially mounted to the drug delivery device 12 as illustrated in FIG. 1, the second piercing end 44 pierces the membrane 18 of the cartridge 14 but the first piercing end 42 does not yet pierce the first or proximal seal 48 of the capsule 46. As such, the first medicament 16 of the cartridge 14 is not in fluid communication with the second medicament 38 contained in the capsule 46.

Figures 2, 3:
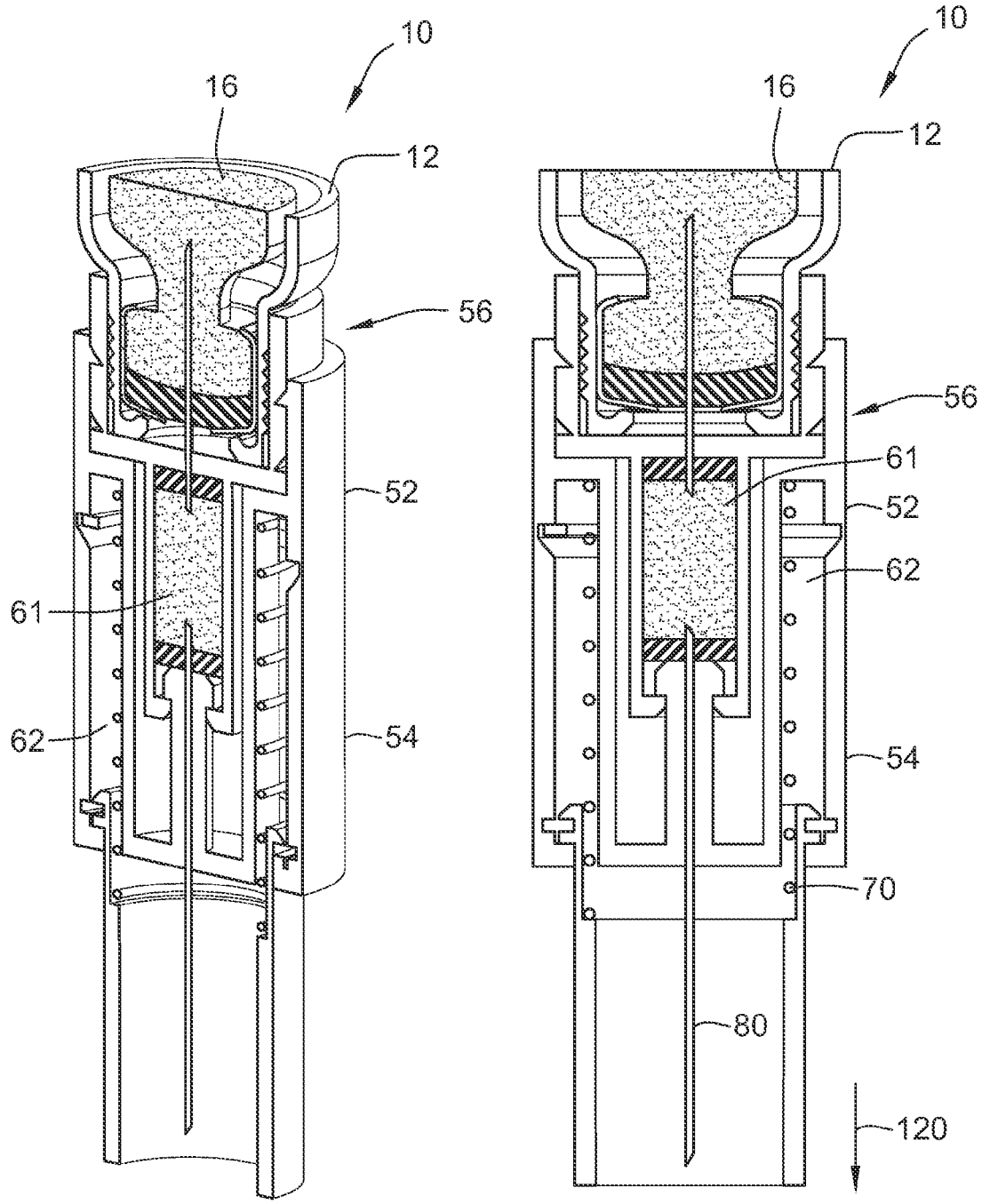
FIG. 2 illustrates a perspective view of the medicated module of FIG. 1 having two needles connected to a reservoir attached to a drug delivery device.
FIG. 3 illustrates a front view of the medicated module of FIG. 2.
Figure 4:
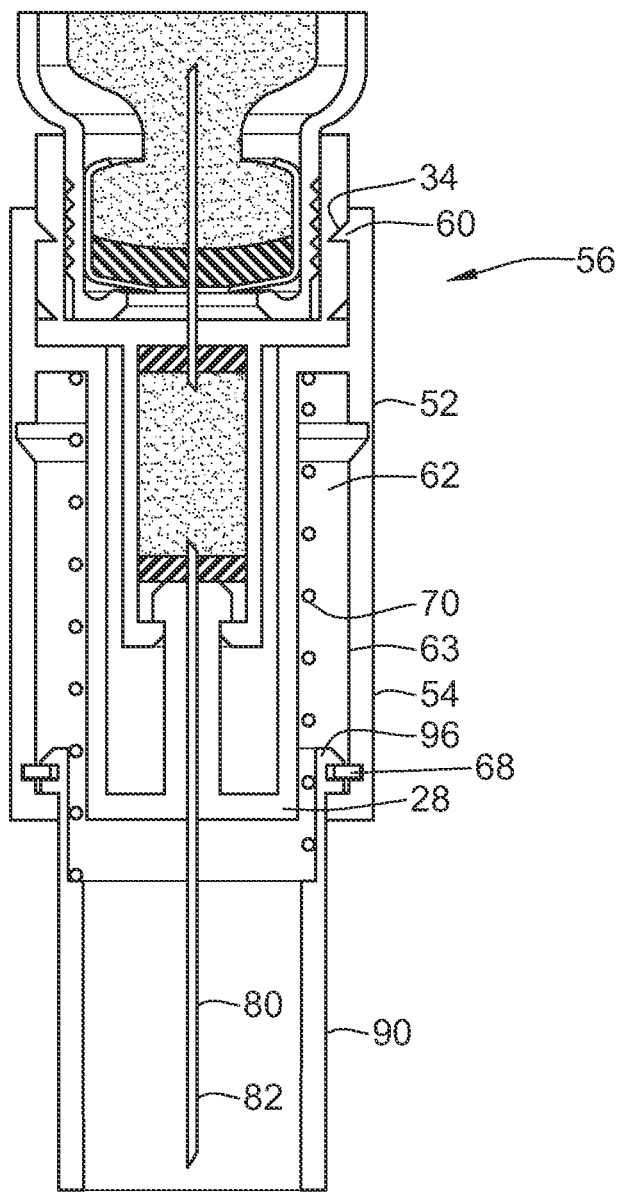
FIG. 4 illustrates the medicated module illustrated in FIG. 1 having a locked out needle guard.

The medicated module 10 further comprises an outer body 52 and preferably this outer body is slidably engaged with the connecting body 24. More preferably, this outer body 52 is slidably engaged with the connecting body 24 and is slidable from an initial position (as illustrated in FIG. 1) to a second or dose injecting position (as illustrated in FIGS. 2 and 3).

The outer body 52 comprises a distal end 54 and a proximal end 56. The outer body proximal end 56 is configured with a male member 60 that releasably engages the connecting body 24. Preferably, when the medicated module is initially mounted onto the drug delivery device 12 as illustrated in FIG. 1, the male member 60 releasably engages the first recess 32 provided along the outer surface 33 of the connecting body 24. In the second or dose injecting position (as illustrated in FIGS. 2 and 3), the male member 60 is moved proximally so that this member engages the second recess 34.

The outer body 52 further comprises a first and a second inner cavity 61, 62 respectively. Preferably, the first inner cavity 61 is formed to contain the reservoir of the connecting body 24 whereas the second inner cavity 62 is formed to contain an elastic member 70, such as a compression spring. As illustrated in FIG. 1, in the initial mounted position of the medicated module, the elastic member 70 is in an extended state. In this extended state, the elastic member resides within this second cavity 62 and between the outer body 52 and the needle guard 90.

The outer body 52 further comprises a distal and a proximal groove 65, 66 provided on inner surface 63. The distal groove 65 includes a movable locking mechanism 68, preferably in the form of a movable circlip. As will be explained below, this movable locking mechanism 68 is used to lock out the needle guard 90 after injection that is, after the needle guard is first moved in a proximal direction and then returned in a distal direction.

The outer body 52 further comprises a second or injection needle 80 rigidly affixed in outer body hub element 64. Preferably, this second needle 80 comprises a double ended needle having a first piercing end 82 (i.e., a distal end) and a second piercing end 84 (i.e., a proximal end).

In this preferred arrangement, when the medicated module 10 is initially mounted to the drug delivery device 12 as illustrated in FIG. 1, the second piercing end 84 does not yet pierce the distal seal 50 of the capsule 46. In addition, in this preferred arrangement, the first piercing end 82 of the second needle 80 is illustrated as being substantially concealed from a user's view by way of the needle guard 90 so as to help reduce any needle anxiety that a patient may be experiencing.

Preferably, needle guard 90 comprises a tubular shaped element and in a relaxed position, as illustrated in FIG. 1, substantially conceals the second needle 80. While substantially concealing the second needle, the needle guard also helps to prevent inadvertent needle sticks. In FIG. 1, this needle guard 90 is illustrated in an unlocked position. That is, during an injection step where a user initiates the injection, the needle guard 90 is free to be moved in a proximal direction or towards the drug delivery device (illustrated by arrow 110 in FIG. 1).

Preferably, the needle guard 90 comprises a plurality of outwardly directed arms 96, 98. These arms 96, 98 are in sliding engagement with an inner surface 63 of the inner cavity 62 of the outer body 52 and reside within the second cavity 62 defined by the outer body. These outwardly directed arms 96, 98 allow for the needle guard 90 to be placed and held in a locked out position after dose injection. In addition, these outwardly directed arms 96, 98 may also serve as a rotation preventor so as to prevent the needle guard from rotating either when it is connected to the drug delivery device or during the medicament injection step.

As illustrated in FIG. 1, the module 10 is shown in a first mounted position on the drug delivery device 12. In this first position, the connecting body 24 is connected to a distal end of the drug delivery device 12. As illustrated, the drug delivery device comprises threads 13 for engagement with the connecting body 24. In one arrangement, the connecting body 24 may comprise a threaded connector to releasably engage these threads. However, in an alternative arrangement, the connecting body 24 may comprise a connector 30 comprising a form fit or snap fit connector arrangement or the like. In this manner, the module 10 may be connected to the drug delivery device 12 merely by sliding the module onto the distal end of the drug delivery device.

As shown in FIG. 1, in this first position, the outer body 52 comprises at a proximal end inwardly extending male members 60 that engage the first recess 32 provided near the proximal end of the connecting body. When the outer body 24 resides in this initial connected position, the inwardly extending male members 60 engage the first set of recesses 32 of the connecting body and both the first and the second needles 40, 80 are not in fluid communication with the medicated module reservoir 36.

As discussed above, in the initial mounting position, both the first and the second needles 40, 80 are not in fluid communication with the medicated module reservoir 36. FIG. 3 illustrates a side view of attachment of the medicated module 10 to the drug delivery device 12 in a dose ready state. To achieve this dose ready state or second state, the outer body 52 is moved in the proximal direction. This outer body proximal movement causes the inwardly extending male members 60 of the outer body to move from the first recess 32 to the second recess 34 of the connecting body.

Importantly, proximal movement of the outer body also causes the distal end 42 of the first needle 40 to penetrate the first pierceable seal 48 of the capsule 46 while the proximal end 44 of the first needle 40 maintains its penetration of the septum of the cartridge 14 of the device 12. Proximal movement of the outer body also causes the proximal end 84 of the second needle 80 to penetrate the second pierceable seal 50 of the capsule 46. Piercing of membranes 48 and 50 opens fluid communication between the first and second medicaments 16, 38 allowing these two medicaments to be dispensed through operation of the dispense mechanism on the drug delivery device 12.

Where the drug delivery device 12 comprises a dose setter 8, a dose of the drug delivery device 12 may then be set using a dose setter 8 (see FIG. 9) in the normal manner (e.g., by dialing out the appropriate number of units). Dispense of the medicaments 16, 38 may then be achieved by subcutaneously injecting the medicaments via activation of a dose button on device 12. The dose button 6 may be any triggering mechanism that causes the dose of the first medicament that was set by the dose setter to move distally towards the distal end of the device. In a preferred embodiment, the dose button is operably connected to a spindle that engages a piston in the primary reservoir of the first medicament. In a further embodiment the spindle preferably is a rotatable piston rod comprising two distinct threads.

During injection, the needle guard 90 is moved in a proximal direction 110 against a force created by the elastic member 70. As the needle guard moves proximally, its outwardly directed arms 96, 98 slide internally within the second cavity 62 of the outer body 52 from the distal groove 65 to the proximal groove 66. Once the outwardly directed arms 96 reach the proximal groove 66, the outwardly directed arms 96 pick up the movable locking feature 68. The first and second medicament 16, 38 may then be injected into an injection site by way of the second needle 80.

After injection and the drug delivery device and the medicated module are removed from the injection site, the needle guard 90 under the force of the biasing element 70 is forced in the distal direction 120. On being forced down or in the distal direction (represented by arrow 120 in FIG. 3) by the force created by the element 70, the needle guard 90 pulls the movable lockout member 68 into the distal groove 65 to thereby lock the needle guard 90 in the down position.

Locking the needle guard 90 in the down position in this manner provides a number of beneficial features. First, it prevents a user from re-using a non-sterile medicated module. Second, the locked needle guard protects and substantially conceals the second needle 80 and therefore reduces the risk of a potential inadvertent needle stick. And third, in substantially concealing the second needle 80, the locked needle guard acts to reduce any potential needle fear, needle phobia or needle anxiety that a patient may experience.

In the arrangements described herein, the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

The connection or attachment between the medicated module as well as the non-medicated module of the described embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The secondary reservoir or capsule can be manufactured from glass or other drug contact suitable material. The integrated injection needle can be any needle cannula suitable for subcutaneous or intramuscular injection.

Preferably the medicated module is provided by a manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. This opening of the seal may be assisted by features such as angled surfaces on the end of the injection device or features inside the module.

Alternatively, the medicated module may be provided in a kit form along where such a kit comprises at least one non-medicated module or a safety needle assembly. There are a number of reasons to provide one or more non-medicated needle assemblies along with a medicated module (such as illustrated in FIG. 1) in a kit form.

For example, there may be a situation where a patient may need to split a dose or top up a dose between two or more drug delivery devices. For example, there may be a situation where a user may need to administer a dose greater than the medicament remaining in the cartridge of the drug delivery device. As just one example, consider that a user might face a situation where they may need to administer a 50 Unit dose and only have only 30 Units remaining in the cartridge of their old (i.e. part-used) drug delivery device. In such a situation, the user would first mount the medicated module onto the drug delivery device, set the drug delivery device to administer 30 Units of the first medicament and then administer the first and the second medicament in a generally known way. Then, because the user would still need to deliver the remaining 20 Units of the first medicament, rather than use another medicated module containing a dose of the second medicament, the user would simply mount a non-medicated module to a new drug delivery device and then administer the remaining 20 Units of the first medicament.

A user may also be faced with administering a large dose of the first medicament and may, for one reason or another, want to split this large dose (i.e., a large volume of medicament) into two or more injections. For example, some users may face themselves administering large doses on the order of 100 Units or more of a single medicament for a single injection. Rather than administer such a large volume of medicament during a single injection, the user may first administer 60 Units while using the medicated module and then administer the remaining 40 Units using a non-medicated module. Splitting up the volume of the administered dose helps to reduce patient discomfort and may reduce potential medicament pooling under the skin. Splitting such a large dose may also be required where there is a mechanical restraint on the drug delivery device in that the device may not be mechanically capable of setting and administering such a large volume of medication.

Another reason that a user may need to split a dose between a medicated and a non-medicated module is that perhaps a physician has instructed a user to split a dose up into two or more injections. Two or more injections may be required if a user experiences certain negative reactions when administering a full dose of a first medicament simultaneously with a second medicated dose. Alternatively, the patient may be instructed to initially administer a first medicament during a specific time of day (e.g., a long acting insulin in the morning) and then later in the day instructed to administer a combination of a first and second medicament (e.g., a long acting insulin in combination with a short acting insulin later in the day). In such a scenario, the non-medicated module could be used to administer the first injection.

Figure 5:
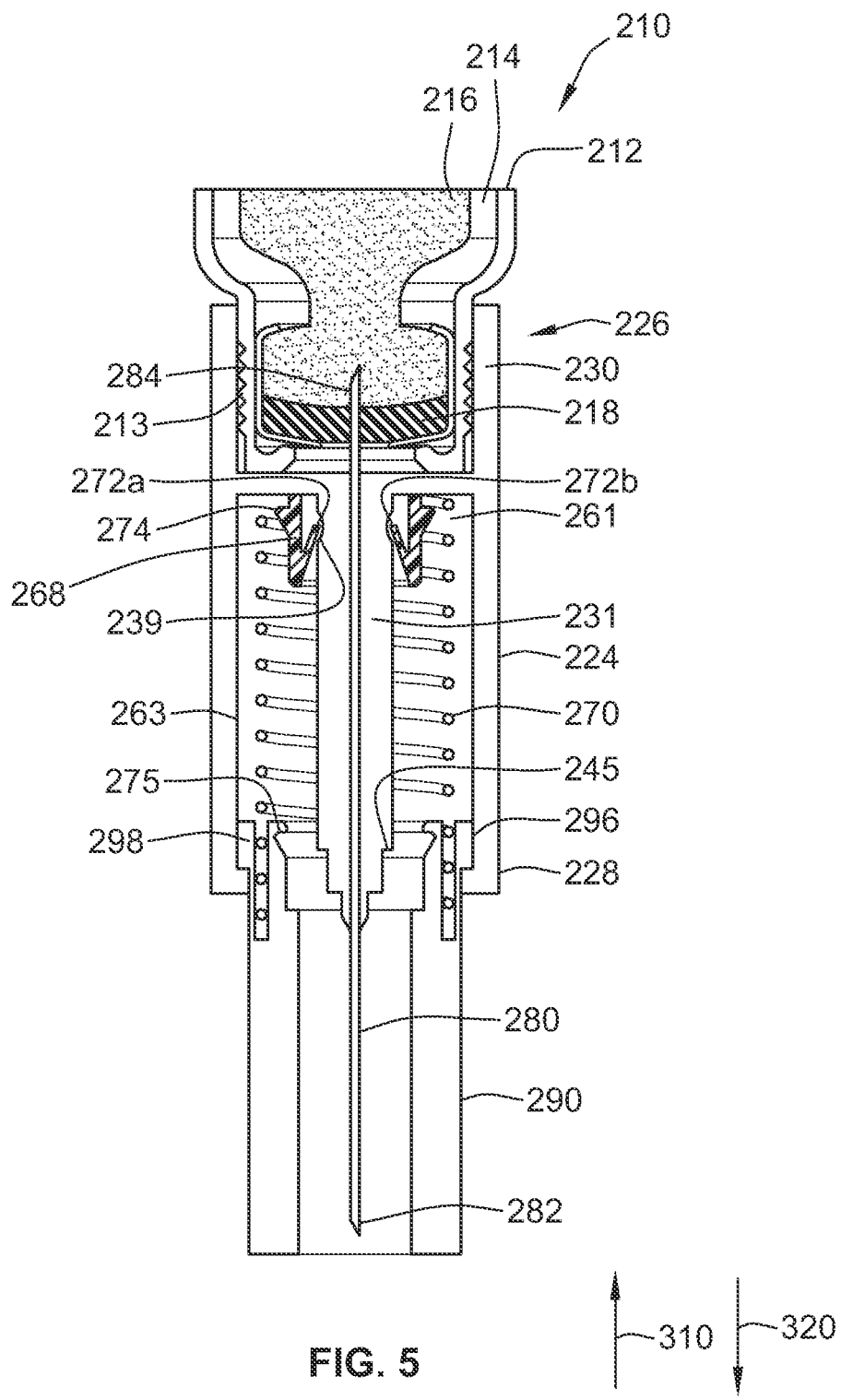
FIG. 5 illustrates a non-medicated module that may be provided in a drug delivery kit that includes the medicated module illustrated in FIG. 1.

FIG. 5 illustrates a first arrangement of a non-medicated module and is somewhat similar in construction to the medicated module. For example, this module 210 comprises a connecting body 224, a double ended needle 280, a biasing member 270, a movable locking member 268, and a needle guard 290.

The connecting body 224 of the module 210 extends from a proximal end 226 to a distal end 228. The proximal end of the connecting body is provided with a connector 230 so that the connector body may be connected to the drug delivery device 212. Preferably, this connector 230 is provided along an inner surface 222 of the connecting body 224 and provides a releasable connection to the drug delivery device 212. Such a releasable connector may comprise a snap fit, form fit, snap lock, screw lock, bayonet fit, luer lock or other similar connection mechanism known to those of skill in the art.

The connecting body 224 further comprises an injection needle 280 rigidly affixed within a main stem 231 of a needle hub. Preferably, this needle 280 comprises a double ended needle having a first piercing end 282 (i.e., a distal end) and a second piercing end 284 (i.e., a proximal end). In this preferred arrangement, when the module 210 is initially mounted to the drug delivery device 212 as illustrated in FIG. 5, the second piercing end 284 pierces the membrane 218 of the cartridge 214.

The connection body 224 further comprises a first inner cavity 261. Preferably, the first inner cavity 261 is formed to contain a movable locking element 268 and a biasing member 270, such as a compression spring. As illustrated in FIG. 5, in the initial mounted position of the needle assembly, the biasing member 270 is in an extended state.

Figure 6:
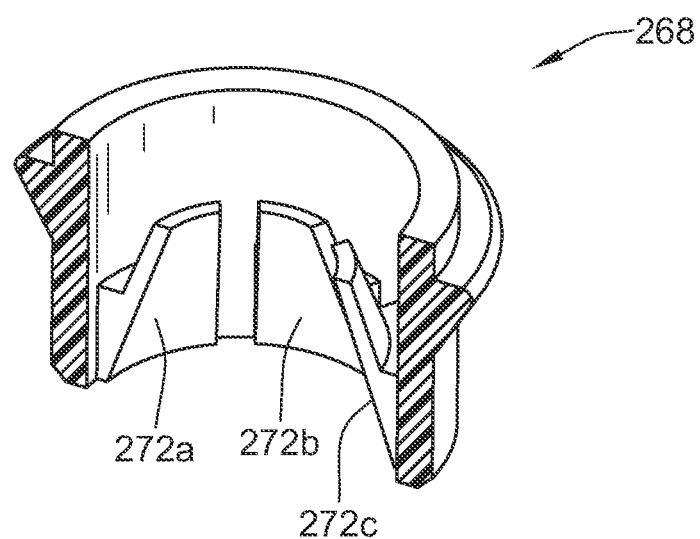
FIG. 6 illustrates a partial view of a movable lockout member of the non-medicated module illustrated in FIG. 5.
Figure 7:
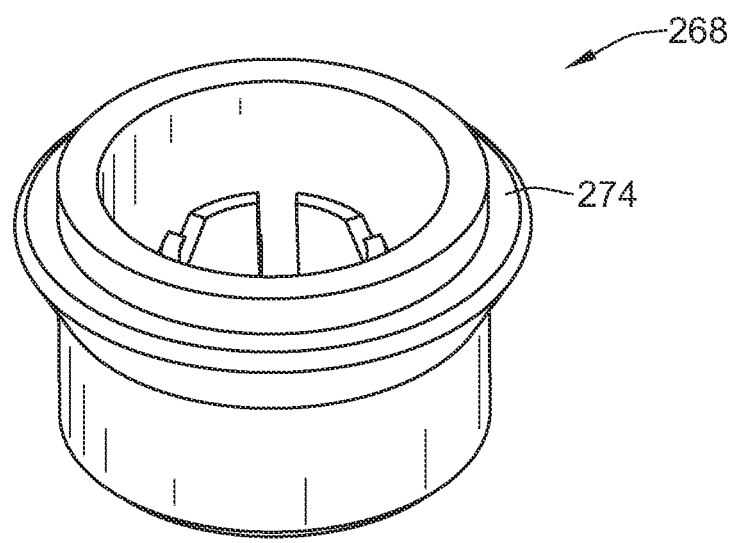
FIG. 7 illustrates a perspective view of the movable lockout member illustrated in FIG. 6.

Details of a preferred arrangement of a locking mechanism can be clearly seen from FIGS. 6 and 7. FIG. 6 illustrates a cross sectional view of the movable locking mechanism 268 and FIG. 7 illustrates a perspective view of the locking mechanism 268. As illustrated, the movable locking mechanism 268 is preferably in the form of a cylindrical shaped member having an outer beveled edge 274. Preferably, the locking mechanism 268 comprises plurality of annular spring fingers 272 a, b, c within the cavity created by the locking mechanism. As illustrated in the first mounted position of FIG. 5, these spring fingers 272 a, b, c engage a recess 239 located on the proximal end 226 of a main stem 231 of the connecting body main hub. The engagement of the spring fingers 272 a, b, c and the recess prevents the locking mechanism from moving in the distal direction prior to injection. This movable locking mechanism 268 is used to lock out the needle guard 290 after an injection has been made. That is, after the needle guard is first moved in a proximal direction and then returned in a distal direction under the force of the biasing member 270.

In this preferred arrangement, when the needle assembly 210 is initially mounted to the drug delivery device 212, the second piercing end 284 of the needle pierces the membrane 218 of the cartridge contained in the drug delivery device 212. The first piercing end 282 of the first needle 280 is illustrated as being substantially concealed from a user's view by way of the needle guard 290. Concealing the needle 280 helps to reduce needle anxiety that a patient may be experiencing while also reducing a potential inadvertent needle stick.

Preferably, the needle guard 290 comprises a tubular shaped element and in a relaxed position, as illustrated in FIG. 5, substantially conceals the needle 280. While substantially concealing this needle, the needle guard also helps to prevent inadvertent needle sticks. In FIG. 5, this needle guard 290 is illustrated in an unlocked position. That is, during an injection step where a user initiates the injection, the needle guard 290 is free to be moved in a proximal direction or towards the drug delivery device. Preferably, the needle guard 290 comprises outwardly directed arms 296, 298 that are in sliding engagement with an inner surface 263 of the inner cavity 261 of the connecting body 224.

As illustrated in FIG. 5, the module 210 is shown in a first mounted position on the drug delivery device 212. In this first position, the connecting body 224 is connected to a distal end of the drug delivery device 212. As illustrated, the drug delivery device comprises threads 213 for engagement with the connecting body 224. In one arrangement, the connecting body 224 may comprise a threaded connector to releasably engage these threads. However, in an alternative arrangement, the connecting body 224 may comprise a connector 230 comprising a form fit or snap fit arrangement or the like. In this manner, the module 210 may be connected to the drug delivery device 212 merely by sliding the module onto the distal end of the drug delivery device.

In this initial mounting position, the needle 280 is in fluid communication with the medicament contained in the cartridge. Where the drug delivery device 212 comprises a dose setter, a dose of the drug delivery device 212 may then be set using a dose setter 212 (see FIG. 9) in the normal manner (e.g., by dialing out the appropriate number of units). Dispense of the medicament 216 may be achieved by subcutaneously injecting the medicaments via activation of a dose button on device 212. The dose button may be any triggering mechanism that causes the dose of the first medicament that was set by the dose setter to move distally towards the distal end of the device. In a preferred embodiment, the dose button is operably connected to a spindle that engages a piston in the primary reservoir of the first medicament. In a further embodiment the spindle preferably is a rotatable piston rod comprising two distinct threads.

During injection, the needle guard 290 is moved in a proximal direction 310 against a force created by the biasing member 270. As the needle guard moves proximally, its arms 296, 298 slide internally within the cavity 261 of the connecting body 224. Once the needle guard beveled edge 275 reaches the rib 274, the beveled edge slips around the rib so that the needle guard 290 picks up the movable locking feature 268. The medicament 216 may then be injected into an injection site by way of the needle 280.

After the injection, the drug delivery device and the module 210 are moved away from the injection site. Then, under the force of the biasing member 270, the needle guard 290 is forced in the distal direction 320. On being forced down or in the distal direction 320 by the force created by the biasing member 270, the needle guard 290 pulls the movable lockout member 268 distally.

Figure 8:
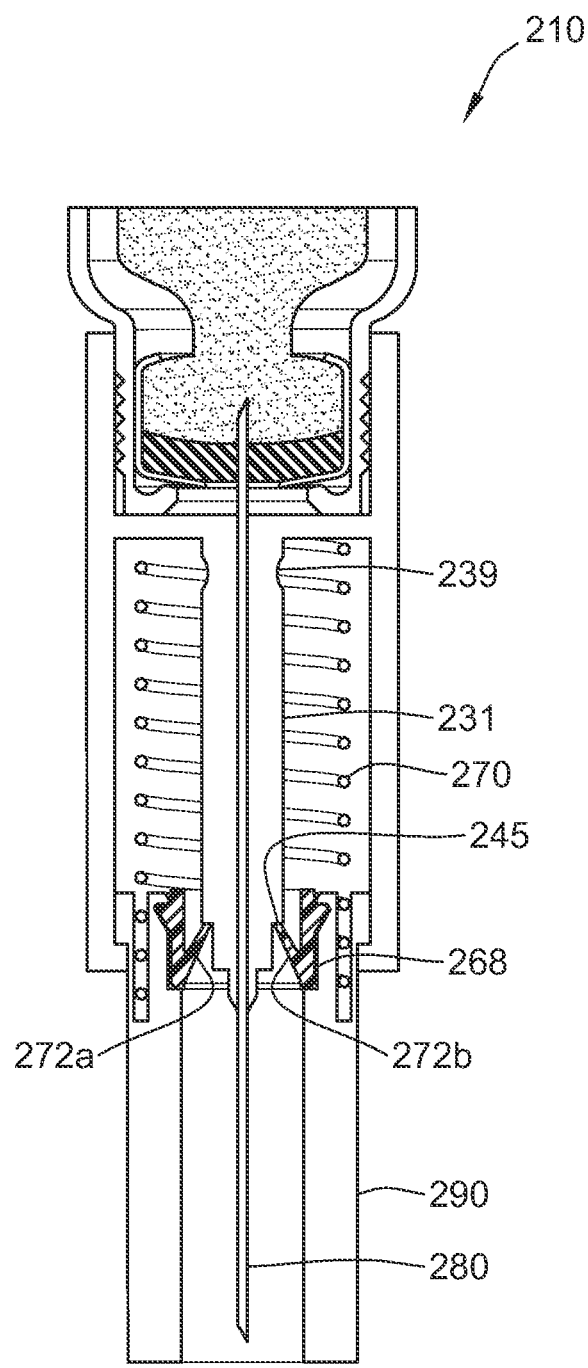
FIG. 8 illustrates a front view of the module illustrated in FIG. 5 having a locked needle guard.

FIG. 8 illustrates the module 210 with the needle guard 290 in a locked position. As illustrated, the annular ring fingers 272 a, b, c of the locking member 268 flex inwardly to as to reside along a first recess 245 provided along the distal end of the main stem 231. As such, the annular ring fingers 272 prevent the needle guard 290 from moving in the proximal direction and therefore prevents a user from re-using the module.

Locking the needle guard 290 in the down position in this manner provides a number of beneficial features. First, it prevents a user from re-using a non-sterile medicated module. Second, the locked needle guard protects and substantially conceals the needle 280 and therefore reduces the risk of a potential inadvertent needle stick. In addition, by substantially concealing the needle 280, the locked needle guard 290 acts to reduce any potential needle fear, needle phobia or needle anxiety that a patient may experience.

The medicated module and the non-medicated module described herein should be designed to operate in conjunction with a multiple use injection device or family of devices, preferably a pen-type multi-dose injection device, similar to what is illustrated in FIG. 9. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A typical injection device contains a cartridge or other reservoir of medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

In certain embodiments where the medicated module contains a single dose of a medicament, the module is attached to a drug delivery device in order to administer the single dose in the reservoir to a patient. In other words, the medicated module cannot be used as a stand-alone injection device. This is because the module does not have a dose delivery mechanism and instead relies on the dose delivery mechanism contained in the drug delivery device to which it is attached.

Exemplary embodiments of the present invention have been described. Those skilled in the art will understand, however, that changes and modifications may be made to these embodiments without departing from the true scope and spirit of the present invention, which is defined by the claims.

We claim:

1. A medicated module attachable to a drug delivery device, said medicated module comprising:
   a connecting body configured for attachment to said drug delivery device; that is configured for setting and delivering a dose of a first medicament;
   an outer body connected to the connecting body such that the outer body can move relative to the connecting body from an initial position to a dose ready position;
   a first needle fixed within said module; where each end of the first needle has a piercing end configured to a pierce a septum or a seal;
   a second needle fixed to the outer body and having a distal end, where the second needle moves with the outer body relative to the connecting body; and
   a needle guard operatively coupled to said module such that the distal end of the second needle is covered prior to using the module and where the guard is slidable relative to the module in a proximal direction;
   a biasing element positioned to bias said needle guard;
   a reservoir containing at least one dose of a second medicament ready for use prior to using the medicated module and is configured to allow the first and second needle to simultaneously come into fluid communication with the second medicament, where the second needle is not in fluid communication with the second medicament when the outer body is in the initial position and where the second needle is in fluid communication with the second medicament when the outer body is in the dose ready position.

2. The module of claim 1 further comprising an outer body operatively coupled to said connecting body wherein the needle guard is operatively coupled to said outer body and wherein the biasing element is positioned between said outer body and said needle guard.

3. The module of claim 1 wherein when said medicated module is moved from an initial position to a dose ready position, said first needle pierces said reservoir and said second needle pierces said reservoir.

4. The module of claim 2 wherein when said medicated module is used to inject a dose of medicament said needle guard moves in a proximal direction to a first position against a force created by said biasing element.

5. The module of claim 4 wherein after said medicated module is used said needle guard moves in a distal direction to a second position because of said force created by said biasing element.

6. The module of claim 5 wherein after said needle guard moves in said distal direction to said second position, said needle guard becomes locked.

7. The module of claim 1 wherein said needle guard is configured to be slidable from an initial position and then to a secondary position and then return to said initial position.

8. The module of claim 7 wherein when said needle guard returns to said initial position, said needle guard substantially conceals said second needle.

9. The module of claim 1 wherein said biasing element comprises a compression spring.

10. The module of claim 1 wherein said medicated module comprises a single dose of medicament.

* * * * *